(12) United States Patent
Wu et al.

(10) Patent No.: US 12,178,946 B2
(45) Date of Patent: Dec. 31, 2024

(54) BLOOD OXYGENATOR

(71) Applicant: UNIVERSITY OF MARYLAND, BALTIMORE, Baltimore, MD (US)

(72) Inventors: Zhongjun Wu, Marriottsville, MD (US); Bartley P. Griffith, Gibson Island, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 664 days.

(21) Appl. No.: 17/380,319

(22) Filed: Jul. 20, 2021

(65) Prior Publication Data

US 2021/0346581 A1 Nov. 11, 2021

Related U.S. Application Data

(63) Continuation of application No. 16/221,761, filed on Dec. 17, 2018, now Pat. No. 11,065,375, which is a
(Continued)

(51) Int. Cl.
| *A61M 1/16* | (2006.01) |
| *A61M 1/36* | (2006.01) |
| *A61M 60/113* | (2021.01) |
| *A61M 60/232* | (2021.01) |
| *A61M 60/38* | (2021.01) |

(52) U.S. Cl.
CPC ........ *A61M 1/1698* (2013.01); *A61M 1/1629* (2014.02); *A61M 1/3623* (2022.05); *A61M 60/113* (2021.01); *A61M 60/232* (2021.01); *A61M 60/38* (2021.01); *A61M 2202/0208* (2013.01); *A61M 2205/3334* (2013.01); *A61M 2205/3368* (2013.01); *A61M 2205/366* (2013.01); *A61M 2206/10* (2013.01); *A61M 2206/16* (2013.01); *A61M 2209/088* (2013.01)

(58) Field of Classification Search
CPC ........ A61M 1/14; A61M 1/16; A61M 1/1698; A61M 1/1629; A61M 60/113; A61M 60/205; A61M 60/50; A61M 2205/3334; A61M 2205/3368; A61M 2205/366; A61M 2206/10; A61M 2206/16; A61M 2209/088
See application file for complete search history.

(56) References Cited

U.S. PATENT DOCUMENTS

| 4,428,934 A | * | 1/1984 | Raible | ..................... A61M 1/32 |
| | | | | 424/529 |
| 4,645,645 A | * | 2/1987 | Martinez | ............... F28F 21/062 |
| | | | | 165/184 |

(Continued)

*Primary Examiner* — Benjamin J Klein
(74) *Attorney, Agent, or Firm* — Whiteford, Taylor & Preston, LLP; Gregory M. Stone (57) ABSTRACT

A blood oxygenator is disclosed comprising a housing, a blood inlet, a blood outlet, a spiral volute, a gas inlet, an oxygenator fiber bundle, and a gas outlet. The housing encloses the fiber bundle and provides the structure for the blood flow path and connectors. The fiber bundle comprises gas-exchange membranes which transfer oxygen to the blood and remove carbon dioxide when the blood flows across the membranes. The spiral volute guides the blood to flow through the fiber bundle. A gas flow chamber receives sweep gas containing oxygen and distributes the sweep gas into the fiber membranes, which gas is then exchanged with the blood being oxygenated.

16 Claims, 11 Drawing Sheets

Related U.S. Application Data continuation of application No. 15/100,871, filed as application No. PCT/US2014/072046 on Dec. 23, 2014, now Pat. No. 10,188,780.

(60) Provisional application No. 61/919,837, filed on Dec. 23, 2013.

(56) References Cited

U.S. PATENT DOCUMENTS

| | | | | |
|---|---|---|---|---|
| 4,902,476 | A * | 2/1990 | Gordon | B01D 63/02 165/184 |
| 4,975,247 | A * | 12/1990 | Badolato | B01D 63/0221 210/321.74 |
| 5,270,004 | A * | 12/1993 | Cosentino | A61M 1/1629 422/46 |
| 6,454,999 | B1 * | 9/2002 | Farhangnia | F28F 21/062 604/6.14 |

* cited by examiner

BLOOD OXYGENATOR

CROSS REFERENCE TO RELATED APPLICATION

This application is a continuation of U.S. patent application Ser. No. 16/221,761 entitled "BLOOD OXYGENATOR," filed with the U.S. Patent and Trademark Office on Dec. 17, 2018, and now U.S. Pat. No. 11,065,375 issued Jul. 20, 2021, which application is a continuation of U.S. patent application Ser. No. 15/100,871 entitled "BLOOD OXYGENATOR," filed with the U.S. Patent and Trademark Office on Jun. 1, 2016, and now U.S. Pat. No. 10,188,780 issued Jan. 29, 2019, which application is a national stage entry of PCT/US2014/072046, filed with the U.S. Patent and Trademark Office on Dec. 23, 2014, which is based upon U.S. Provisional Patent Application Ser. No. 61/919,837, filed with the U.S. Patent and Trademark Office on Dec. 23, 2013, by the inventors herein, the specifications of which are incorporated herein by reference.

GOVERNMENT LICENSE RIGHTS

This invention was made with government support under Grant Numbers HL082631 and HL118372 awarded by the National Institutes of Health. The government has certain rights in the invention.

FIELD OF THE INVENTION

This invention relates generally to blood oxygenator devices and methods of their use, and more particularly to blood oxygenators that provide uniform flow and oxygenation.

BACKGROUND

Hollow fiber membrane blood oxygenators are the current gold standard for blood oxygenation. These oxygenators typically incorporate one of four blood flow path configurations, as summarized in U.S. Pat. No. 5,462,619: (1) longitudinal (axial) flow through an annular bundle (see U.S. Pat. No. 4,975,247); (2) circumferential flow around an annular bundle (see U.S. Pat. No. 3,794,468); (3) transverse flow across a bundle of substantially rectangular cross-section (see U.S. Pat. No. 5,188,801); and (4) radially outward flow through an annular bundle (see U.S. Pat. No. 3,422,008). The specifications of the foregoing are incorporated herein by reference in their entireties.

Although the membrane blood oxygenators based on the above principles are generally acceptable for cardiopulmonary bypass during open heart surgeries, they have a number of problems when they are used for respiratory support over longer durations (e.g., days to weeks). They have a relatively large blood-contacting surface area, a large prime volume, and a large physical size with very limited long-term biocompatibility and durability. The drawbacks of these oxygenators are associated with inherent blood fluid dynamics within these oxygenators, including non-uniform blood flow through the fiber membranes, the existence of laminar boundary flow zones between the blood cells and fiber membranes, and large physical size.

The non-uniform blood flow across the fiber membranes results in hyper- and hypo-perfusion of blood in the flow path. Hyper-perfusion does not have any additional benefit once blood is oxygen-saturated. In order to assure that all blood cells in the hypo-perfusion region are well oxygenated, longer flow paths are needed, thus resulting in extended blood contact with the fiber membrane surfaces and a large surface area of the fiber membranes. When blood flows through fiber membranes, a relatively thick blood boundary layer is developed. The blood boundary layer that is formed increases the resistance to oxygen diffusion to blood cells that are not directly in contact with the fiber membrane surface. The gas transfer efficiency can be significantly hindered by the existence of the boundary layer. Therefore, gas exchange membrane surface areas of 2 to 4 $m^2$ and a large prime volume are typically required to provide the needed gas exchange. The non-uniform blood flow can potentially induce excessive mechanical shear stresses or stasis in the blood flow path in the oxygenators. These are the major contributing factors to blood activation and thrombosis formation, resulting in limited long-term biocompatibility and durability. In addition, the large physical size also limits the wearability for ambulatory respiratory support.

In recognition of the drawbacks related to the boundary layer zones in the foregoing patents, methods to decrease the boundary layer effect have been proposed by increasing the shear rate and/or turbulence of the blood flow path by introduction of secondary flows. The blood is directed to flow perpendicular or at a substantial angle to the fiber membranes. Examples of this type of design include those described in U.S. Pat. No. 4,639,353 (Takemura) and U.S. Pat. No. 5,263,924 (Mathewson), the specifications of which are incorporated herein by reference in their entireties. Takemura describes the arrangement of bundles of hollow fibers perpendicular to the direction of blood flow via a series of flow guide structures. Mathewson describes the integrated centrifugal pump and membrane oxygenator in which the hollow fibers are displaced circumferentially in a ring around an impeller of the centrifugal pump. The blood is pumped through the hollow fibers for oxygenation. One drawback of Mathewson's design is that there exist potential stagnant flow zones between the annular fiber bundle and the outer housing wall.

To overcome shortcomings of the prior art in terms of non-uniform blood flow path and less biocompatibility, a rotating impeller was introduced to generate uniform blood flow through an annular fiber bundle, as described in U.S. Pat. No. 8,496,874. The use of an integrated rotating impeller to achieve uniform blood flow may be beneficial. However, integration of the pump with a blood oxygenator into a system can introduce difficulties for manufacturing and complex flow paths in the integrated system.

In consideration of the limitations of the foregoing devices, there is a need for a compact, efficient and non-traumatic blood oxygenator with a low prime volume and a small surface area of gas exchange membranes.

SUMMARY OF THE INVENTION

Disclosed is a unique blood oxygenator that addresses one or more of the shortcomings of the prior art. More particularly, a blood oxygenator is provided herein having unique blood flow distribution control, resulting in a significant reduction of membrane surface area and priming volume, and reduced trauma when compared with currently known oxygenator technologies. Techniques are also provided for a blood oxygenator device that provides one or more advantages over currently available blood oxygenators. In various embodiments, the device provides long-term durability and reliability, and can be used for, among other applications, cardiopulmonary bypass during cardiothoracic surgeries, extracorporeal membrane oxygenation (ECMO) for cardiopulmonary support or respiratory support in hospitals, and ambulatory ECMO.

In accordance with certain aspects of an embodiment of the invention, a blood oxygenator includes a housing, a blood inlet, a blood outlet, a spiral volute, a gas inlet, an oxygenator fiber bundle, and a gas outlet. The housing encloses the fiber bundle and provides the structure for the blood flow path and connectors. The fiber bundle comprises gas-exchange membranes that transfer oxygen to the blood and remove carbon dioxide when the blood flows across the membranes. The spiral volute guides the blood to flow through the fiber bundle. The gas flow chamber receives sweep gas containing oxygen and distributes the sweep gas into the fiber membranes.

With regard to further aspects of an embodiment of the invention, a heat exchanger is integrated into the blood oxygenator. The heat exchange element is located between an annular space and the fiber bundle.

With regard to still further aspects of an embodiment of the invention, a kit is provided that includes both a blood oxygenator and a blood pump. The kit may be specifically configured for ambulatory cardiopulmonary and respiratory support.

Still other aspects, features, and advantages of the invention will be readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE FIGURES

The above and other features, aspects, and advantages of the present invention are considered in more detail, in relation to the following description of embodiments thereof shown in the accompanying drawings, in which.

DETAILED DESCRIPTION

The invention summarized above may be better understood by referring to the following description, claims, and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form. Likewise, in the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Figure 1:
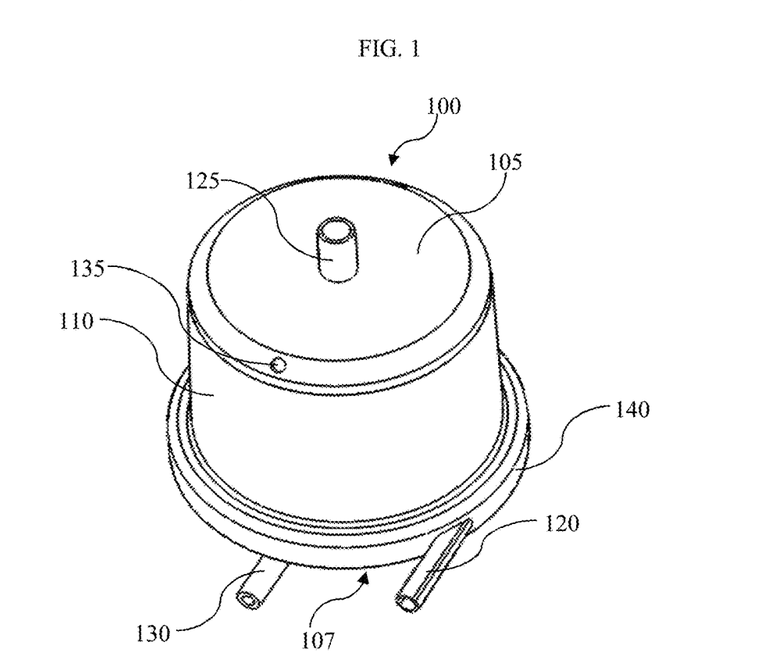
FIG. 1 is a perspective view of a blood oxygenator in accordance with certain aspects of an embodiment of the invention.

A device, system, and method are described herein for a blood oxygenator. The exterior of a blood oxygenator 100, as shown on FIG. 1, comprises a housing 110 having a top 105 and a bottom 107. The top 105 of the housing 110 has a blood outlet 125. In some exemplary embodiments, the top 105 of the housing includes a gas exhaust port 135 and, in some instances, may include a vent port 137 on housing 110 (shown on FIG. 2). The bottom 107 of the housing 110 has a blood inlet 120 and, in some exemplary embodiments, a gas inlet 130.

Figure 2:
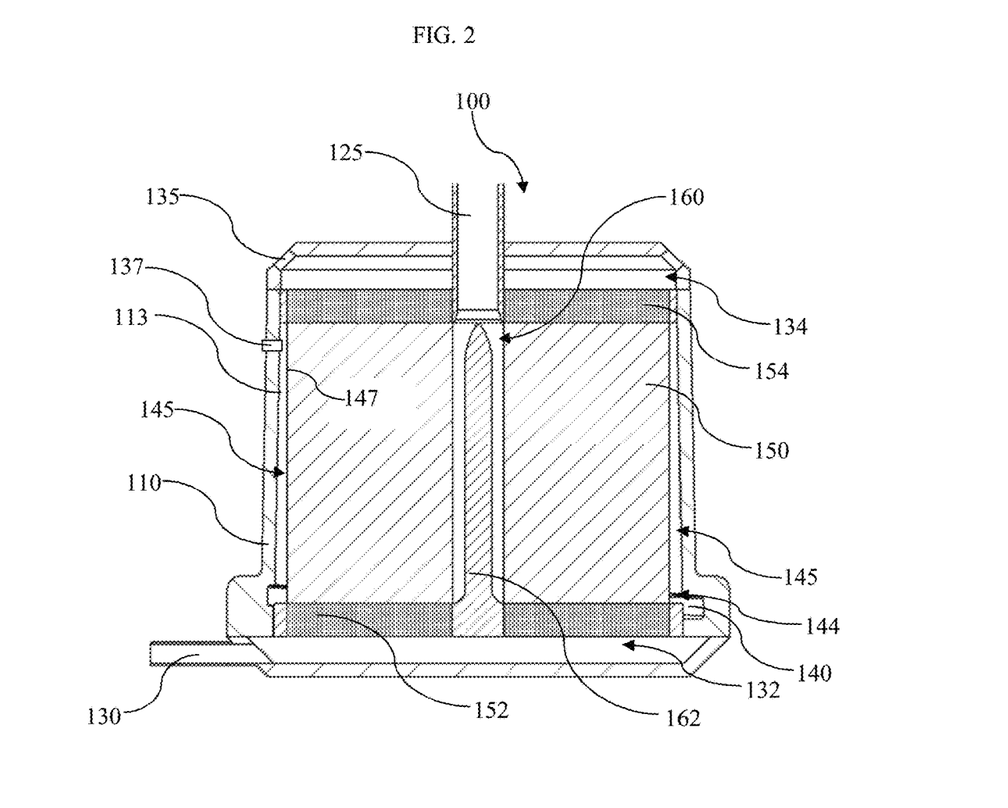
FIG. 2 is a cross-sectional view of the blood oxygenator of FIG. 1.

The housing 110 encloses the internal elements of blood oxygenator 100, as depicted in FIG. 2, including the oxygenator fiber bundle 150, and provides the structure for the blood flow path and connectors. The blood inlet 120 on the bottom 107 of the housing 110 is connected to a spiral volute 140. As used herein, the phrase "spiral volute" refers to a spiral or helical flow path formed in a cylindrical annulus between the outer, typically cylindrical, surface of the fiber bundle and an inner surface of the housing. The cross-sectional area of the flow path will generally be at a maximum at an inlet end of the flow path, and will decrease toward the outlet end in order to at least partially offset the reduction in flow velocity that would otherwise occur as the blood flows from the flow path into the fiber bundle.

Figure 3:
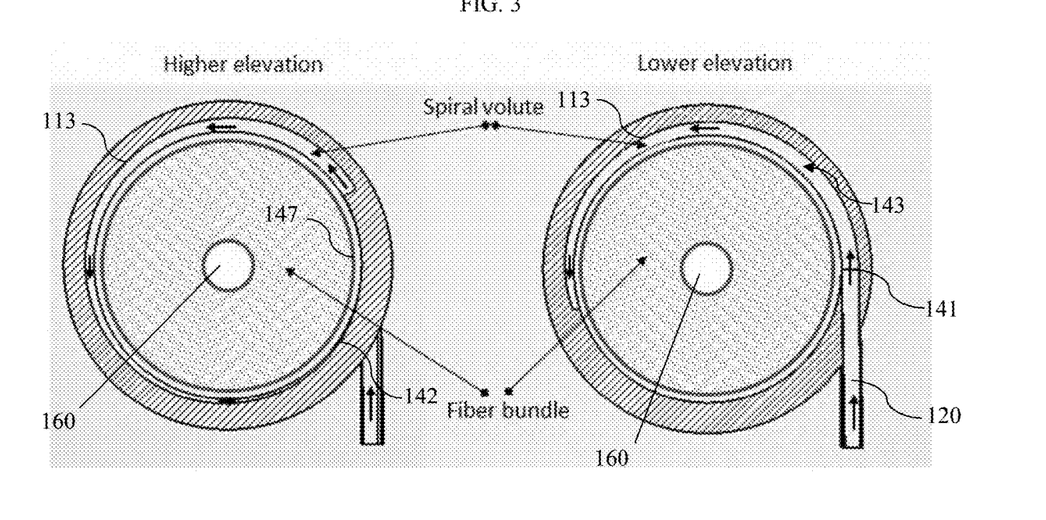
FIG. 3 is a schematic representation of blood flow in the spiral volute of the blood oxygenator of FIG. 1 at two elevations.
Figure 4:
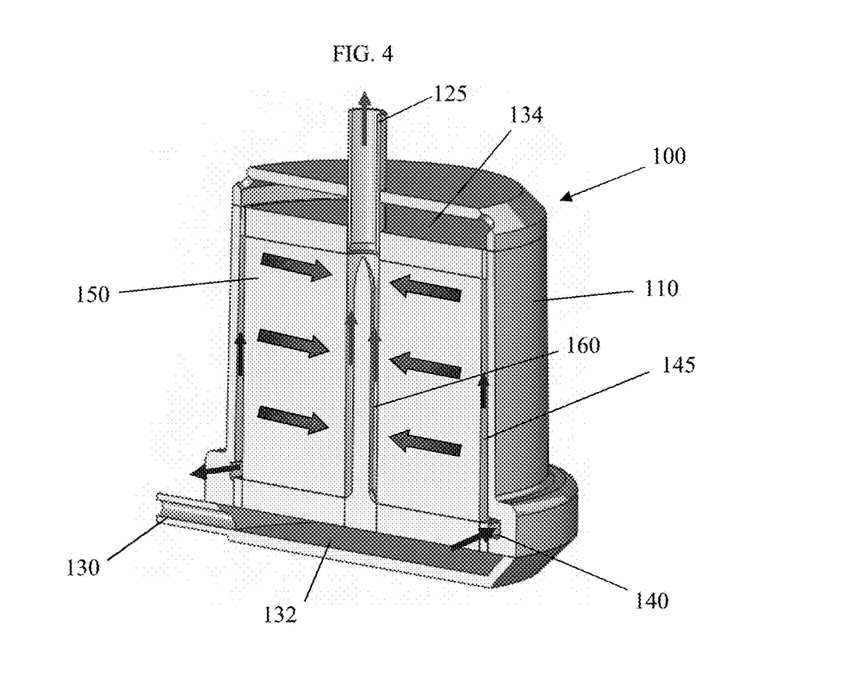
FIG. 4 is a schematic representation of a blood flow path in the spiral volute and the fiber bundle of the blood oxygenator of FIG. 1.

The spiral volute 140 has a first end 141 (shown in the lower elevation of FIG. 3) and a second end 142 (shown in the higher elevation of FIG. 3). The blood inlet 120 connects with the spiral volute 140 at the first end 141. The channel extending between first end 141 and second end 142 of the spiral volute 140 defines an internal cavity 143 that decreases in size from the first end 141 to the second end 142. As shown in FIG. 3, as the internal cavity 143 of spiral volute 140 decreases in size, it also moves up in elevation in a spiral formation. In addition to an internal cavity 143, the spiral volute 140 has an aperture 144 that connects the internal cavity 143 to an annular space 145 between an inner wall 113 of housing 110 and an outer surface 147 of an oxygenator fiber bundle 150 in blood oxygenator 100, as shown in FIGS. 2 and 4. The aperture 144 allows blood to enter the annular space 145 from the internal cavity 143.

A uniform blood flow path across the membranes in the fiber bundle 150 is achieved by the spiral volute 140. The blood is guided by the blood inlet 120 into the spiral volute 140 which gradually discharges the blood circumferentially (360 degree) into the annular space 145 between the inner wall 113 of the housing 110 and outer surface 147 of fiber bundle 150. Annular space 145 is generally in the shape of a cylinder, the outer perimeter of which preferably conically tapers inward as the annular space 145 extends away from spiral volute 140. Spiral volute 140 extends circumferentially around the interior of housing 110 and has a gradually decreasing radius as it extends spirally upwards. The aperture 144 of the spiral volute 140 that opens into the cylindrical annular space 145 is progressively increased and finally merges into the annular space 145. Further, the aperture 144 of the spiral volute 140 preferably merges into the annual space about 300° from the first end 141; i.e., the second end 142 is at a position 300° from the first end 141.

Fiber bundle 150 preferably comprises a cylindrical annulus composed of thousands of microporous hollow fibers with pore sizes of less than 0.1 micron. The membrane fibers are commercially available and range in size from 250 to 400 micron outside diameter with a wall thickness of approximately 30 to 50 microns thick. The fiber membranes may or may not include an anti-thrombogenic coating containing heparin or a functional equivalent attached to the outside of each fiber. The porosity (void ratio) of the fiber bundle 150 is determined according to the desired pressure loss across the fiber bundle, typically ranging from 0.4 to 0.7. Alternatively, coated or skinned hollow fibers may be utilized, which permit oxygen and carbon dioxide diffusion through a non-porous skin layer of the outer wall of the fibers. The fibers are typically commercially available in a tape configuration whereby individual fibers are arranged to a predetermined configuration (e.g., parallel straight or bias, multi-directional, woven, spaced, etc.) permitting tape wrapping to form a cylindrical or conical-like bundle configuration. Alternatively, the fiber can be wrapped or wound like a spool of kite-string.

The ends of the fiber bundle 150 are cast potted in a polymer (e.g., urethane) to form upper potting 154 and lower potting 152. The bundle ends are trimmed at upper potting 154 and lower potting 152 to open the internal passages of the hollow fibers. It is through these inner lumens that the sweep gas is distributed. The fiber bundle 150 is affixed onto the housing at the lower potting 152 and upper potting 154. The blood and gas are structurally separated by the lower potting 152 and the upper potting 154.

As shown in FIG. 2, the fiber bundle 150 is configured to allow blood to move from the outer surface 147 of fiber bundle 150 through the internal passages of the hollow fibers into a central lumen 160. The central lumen 160 is configured to receive blood that travels through fiber bundle 150. The upper end of lumen 160 communicates with blood outlet 125. Thus, blood travels from the outer surface 147 of the oxygenator fiber bundle 150 through the oxygenator fiber bundle 150, into the central lumen 160, and out of the housing 110 through the blood outlet 125. Guide structure 162 may optionally be provided within central lumen 160 to help channel the blood out of the blood oxygenator 100. The guide structure 162 extends orthogonally from the bottom 107 of housing 110.

Gas inlet 130 is preferably located in bottom 107 of housing 110. Gas inlet 130 communicates with lower gas flow chamber 132 which allows for the distribution of the gas into the fiber membranes of the fiber bundle 150. An upper gas flow chamber 134 located on the top 105 of the housing 110 receives the expelled gas from the fiber membranes and allows for the gas to exit gas exhaust port 135.

Blood oxygenator 100 preferably also includes a vent port 137, as shown in FIG. 2, positioned within housing 110 at the location at which air bubbles are likely to accumulate. It is important to be able to remove gaseous bubbles from the blood oxygenator 100 during use. Bubbles typically result from trapped air failing to adequately de-bubble during priming, broken membrane fibers, or excessive negative pressure applied to the blood drawing gas out of solution.

Figure 5A:
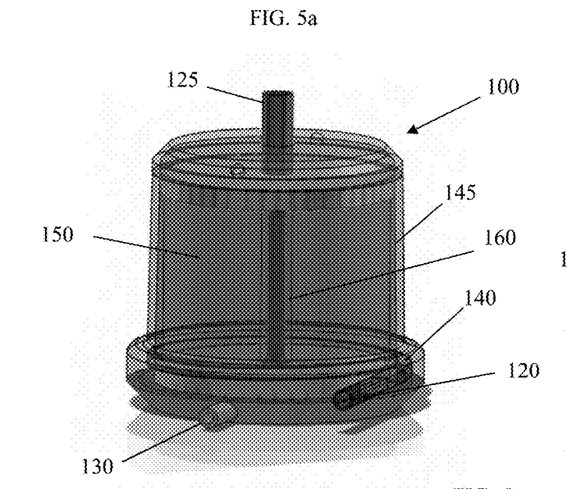
FIG. 5a is a transparent view showing various elements of the blood oxygenator of FIG. 1, and FIG. 5b provides the same transparent view and includes a schematic representation of a blood flow path through the blood oxygenator of FIG. 1.
Figure 5B:
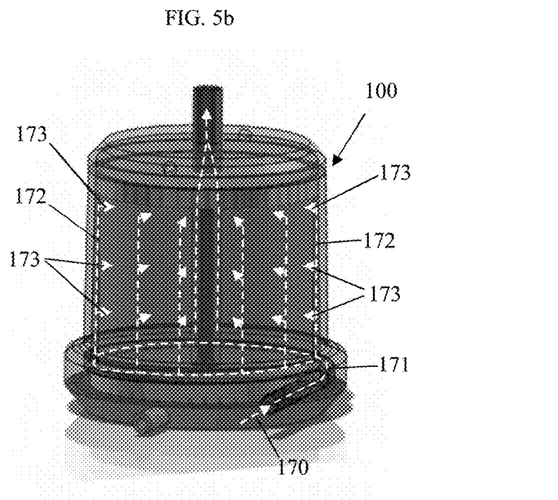

FIG. 5a provides a transparent view of the blood oxygenator showing the above components in a fully assembled blood oxygenator 100. FIG. 5b shows the same transparent view, and also shows a schematic representation of a blood flow path through blood oxygenator 100. More particularly, first segment 170 shows the path in which blood enters blood oxygenator 100, from which it travels into the spiral volute along spiral flow path segment 171. From the start of opening 144 to the end of spiral volute 140, blood likewise flows upward in the direction of flow lines 172 from spiral volute 140 and into annular space 145 in a continuous, vertical flow path extending circumferentially around fiber bundle 150. As blood flows upward in the direction of flog lines 172, it likewise flow radially inward in the direction of flow lines 173 and toward central lumen 160, and then upward through central lumen 160 and out through blood outlet 125.

Figure 6:
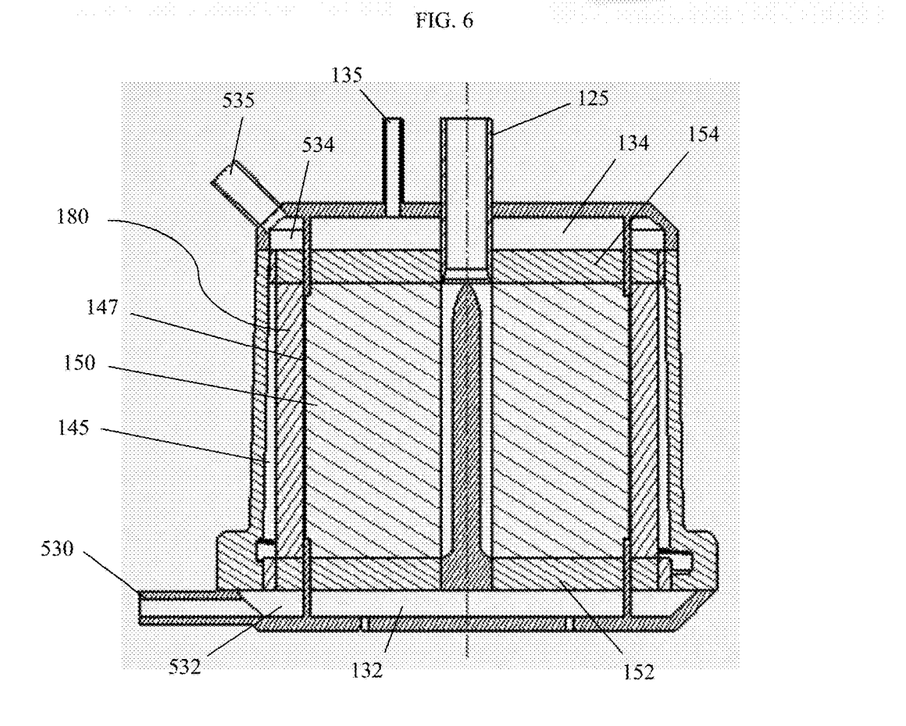
FIG. 6 is a cross-sectional view of the blood oxygenator of FIG. 1 and further comprising a heat exchanger.

Blood oxygenator 100 may also optionally provide a heat exchange function. As shown in FIG. 6, an optional heat exchange element 180 is provided in the form of a cylindrical annulus around the fiber bundle 150. The heat exchange element 180 is located between the outer surface 147 of the fiber bundle 150 and the annular space 145. The heat exchange element may be comprised of capillaries formed together to construct a cylindrical annulus, and potted together with the fiber bundle. The heat exchange element capillaries can either be made of biocompatible metals or polymers. After being potted, the lumen of the capillaries can be opened using the same approach as for the hollow fibers of fiber bundle 150. A separate flow path through the heat exchange element capillaries is provided. In this configuration, enclosed chambers are disposed in the housing above the upper potting 154 and below the lower potting 152. A first chamber 134 is provided above the upper potting 154 for the sweep gas and is in fluid communication with exit gas exhaust port 135, while a second chamber 534 is provided above the upper potting 154 and is in fluid communication with exhaust port 535 for the heat transfer medium. Likewise, a first chamber 132 is again provided below the lower potting 152 for the sweep gas and is in fluid communication with gas inlet 130 (not shown in FIG. 5), while a second chamber 532 is provided below lower potting 152 and is in fluid communication with an inlet 530 for supply of the heat transfer medium. When the heat transfer medium and sweep gas flow through the capillaries of the heat exchanger and the fiber membranes, respectively, the blood is heated and controlled for temperature, the oxygen is transferred to the blood, and carbon dioxide is removed from the blood while the blood radially flows through the heat exchange element 180 and the fiber bundle 150. Other means for heating the blood may also be used without departing from the spirit or scope of the invention. For example, a portion of the oxygen fibers may be substituted with fibers that enable heat exchange. Such a configuration would also utilize hollow tube(s), the inside of which could flow temperature controlled water or other fluid to affect blood temperature change and/or maintenance.

Figure 7:
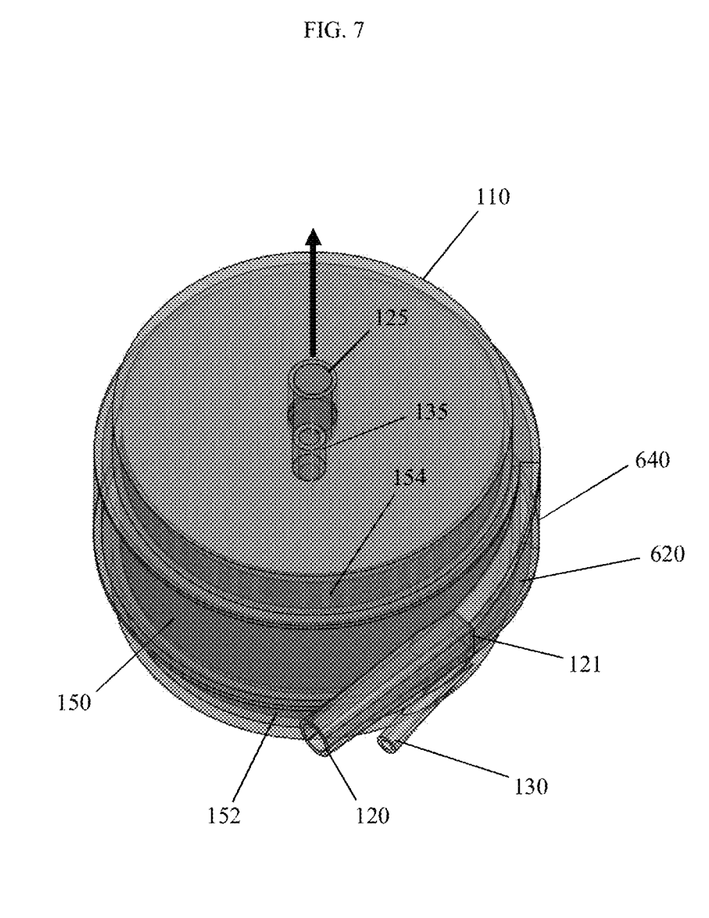
FIG. 7 is a perspective view of a blood oxygenator in accordance with further aspects of an embodiment of the invention.

As shown in FIG. 7, blood may alternatively enter into housing 110 through a flow path that is adjacent to the mid-section of fiber bundle 150, and need not enter housing 110 through the bottom of housing 110. More particularly, and with reference to FIGS. 7 through 10, housing 110 may include a top housing section 602, a bottom housing section 604, and a mid-housing section 610. While each of such housing sections are generally cylindrical in form, top housing section 602 and bottom housing section 604 preferably have the same diameter, and moreover are configured alike to the corresponding portions of housing 110 shown in FIG. 2, while mid-housing section 610 has a wider diameter so as to incorporate spiral volute 640. Bottom housing section 604 includes gas inlet 130 configured as described above, with first chamber 132 in communication with gas inlet 130 to receive the sweep gas.

Likewise, fiber bundle 150 is provided inside of housing 110, and is positioned so that lower potting section 152 of fiber bundle 150 is positioned within bottom housing section 604, upper potting section 154 of fiber bundle 150 is positioned within top housing section 602, and the central gas exchange portion of fiber bundle 150 is positioned within mid-housing section 610. Top housing section 602 also includes gas exhaust port 135 configured as described above, and blood outlet 125 configured as described above and in communication with an internal, central lumen 160 which may optionally include a guide structure 162, again all configured as described above.

Figure 8:
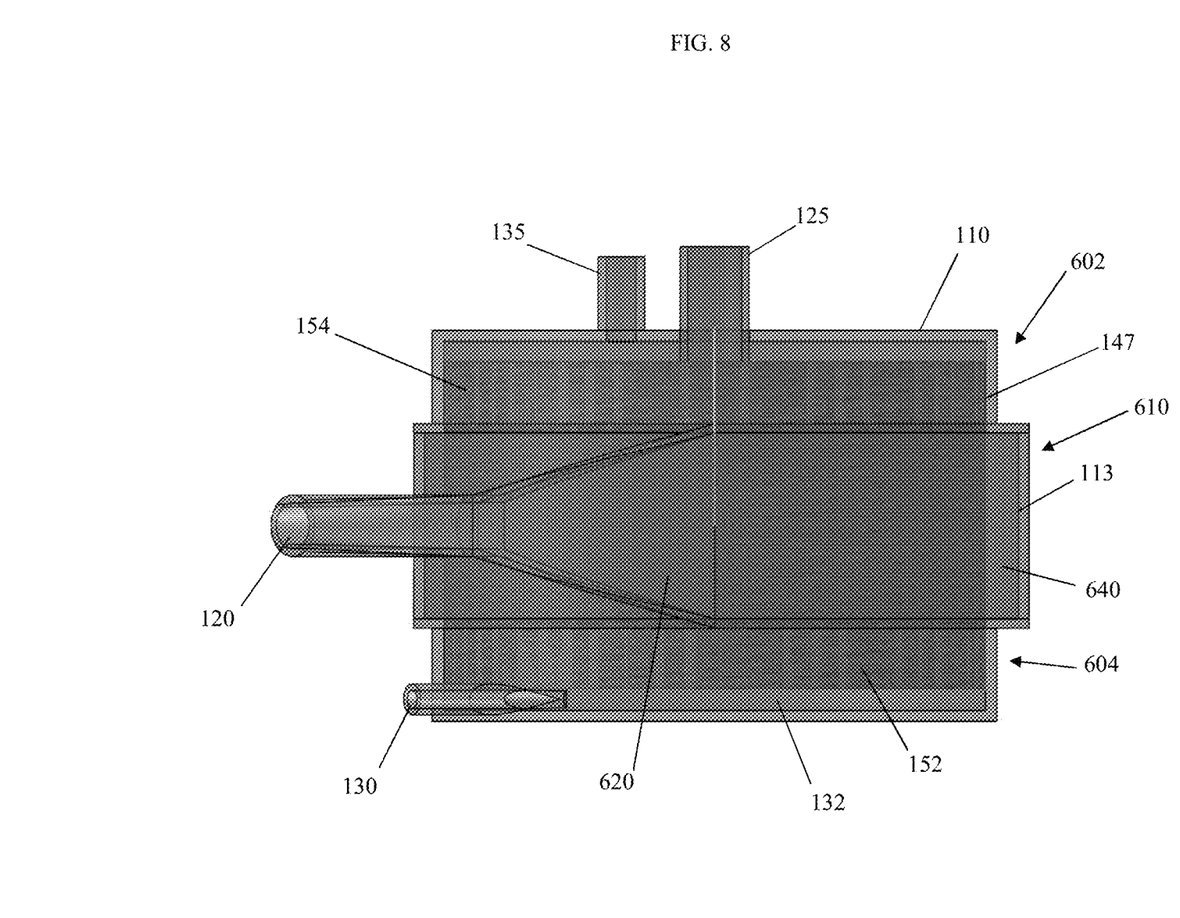
FIG. 8 is a side, cross-sectional view of the blood oxygenator of FIG. 7.

With particular reference to FIGS. 7 and 8, the spiral volute 640 is positioned in the space between the outer surface 147 of fiber bundle 150 and the inner wall 113 of housing 110. As shown in FIG. 8, circular blood inlet 120 is positioned in the middle of mid-housing section 610. At the inner end 121 of blood inlet 120, the blood flow bath begins to vertically widen, expanding into the full vertical height of spiral volute 140 (generally equal in dimension to the radially absorptive portion of fiber bundle 150) through a transitional area 620. While transitional area 620 vertically expands the blood flow path, it likewise progressively narrows that flow path by narrowing the gap between the outer surface 147 of the fiber bundle 150 and the inner wall 113 of housing 110, as best shown in the top-down, sectional view of FIG. 9.

Figure 9:
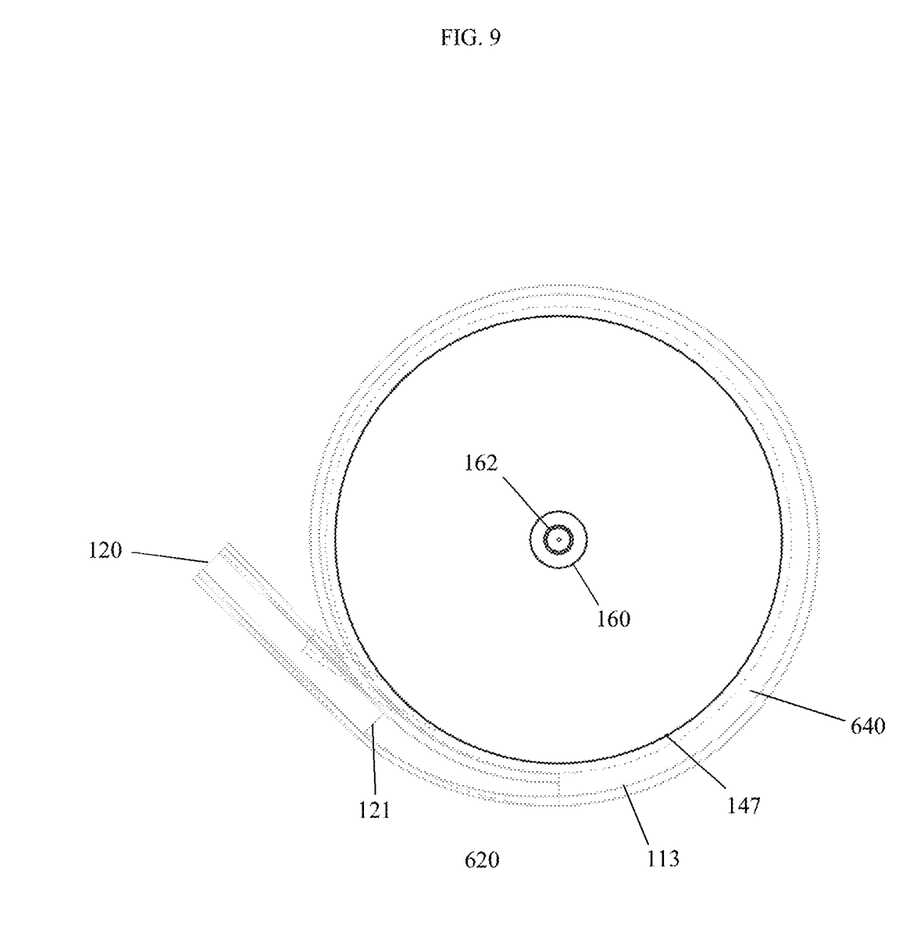
FIG. 9 is a top, cross-sectional view of the blood oxygenator of FIG. 7.
Figure 10:
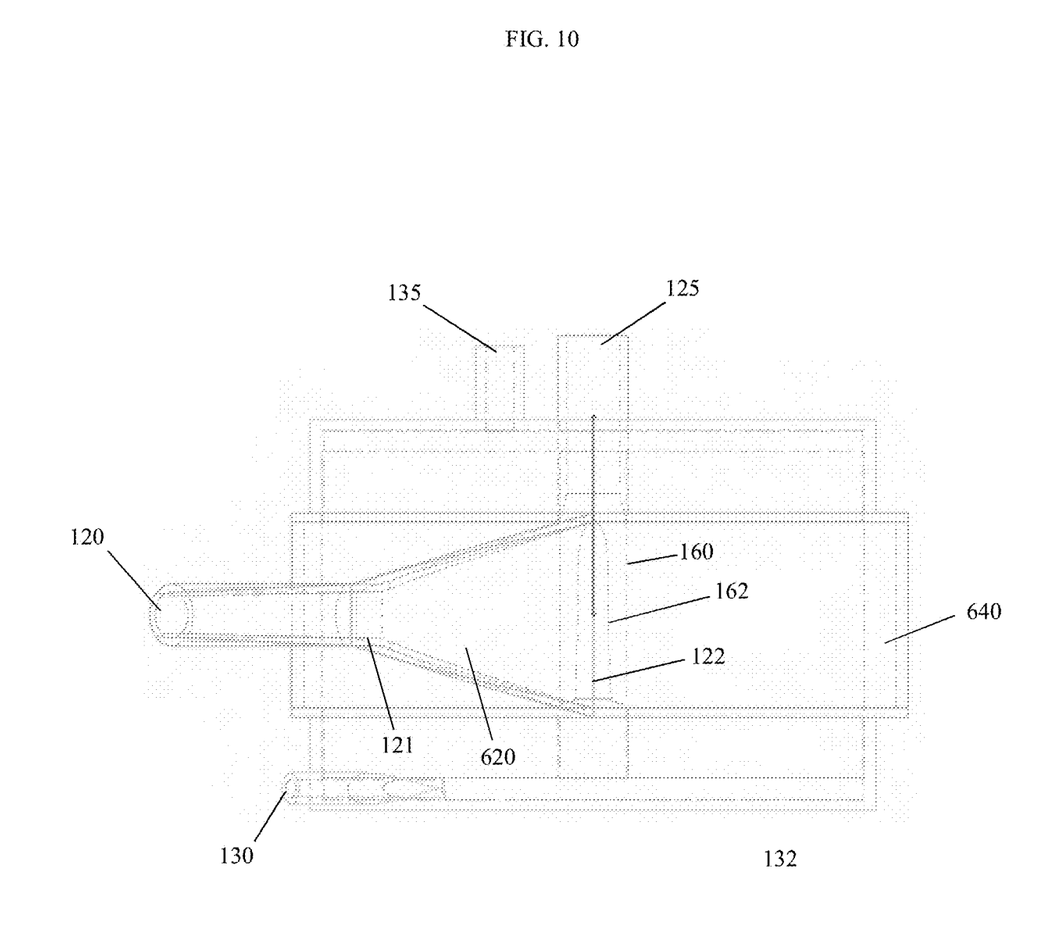
FIG. 10 is a side, cross-sectional view of the blood oxygenator of FIG. 7.

With continued reference to FIG. 9, at the end of spiral volute 640 (i.e., after 360° from the interior end 122 of transitional area 620), the inner wall 113 of housing 110 is nearly contiguous with the outer surface 147 of fiber bundle 150. Thus, blood entering through blood inlet 120 and passing therefrom into transitional area 620 diverges as it passes through transitional area 620, and from transitional area 620 enters into the spiral volute 640 to begin circulation around fiber bundle 150. Moreover, as blood circulates through spiral volute 640 around fiber bundle 150, a portion of the blood volume that is in contact with the fiber bundle 150 enters radially into the porous fiber bundle while the portion of the blood volume that is closer to the inner wall 113 of housing 110 continues its circumferential flow around the fiber bundle 150, until it eventually enters fiber bundle 150. In this configuration, the uniform blood flow across fiber bundle 150 is achieved 360° around fiber bundle 150 and from the bottom to the top of the fiber bundle 150.

Figure 11:
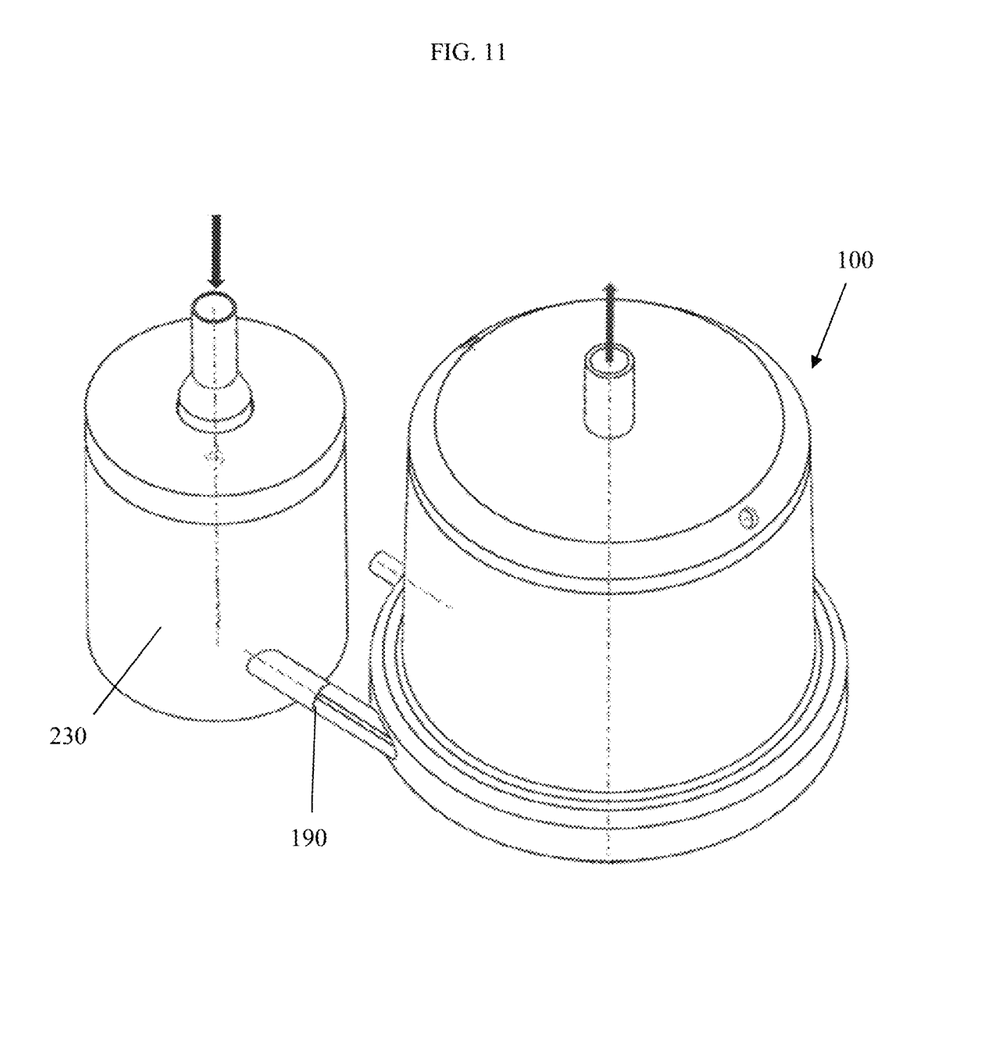
FIG. 11 is a perspective view of the blood oxygenator of FIG. 1 detachably attached to a blood pump.

As shown in FIG. 11, the blood oxygenator 100 may be connected to a blood pump 230. Pump 230 is connected to the blood inlet of blood oxygenator 100, such as through a quick connector 190 of standard configuration. Furthermore, pump 230 and blood oxygenator 100 may be provided together as a kit. It is contemplated that the kit may comprise the various elements required for the blood oxygenator 100 to function. Such kits may be particularly useful for ambulatory cardiopulmonary and respiratory support. In certain configurations, blood pump 230 and blood oxygenator 100 can both be contained within housing 110 in a single unit.

Figure 12:
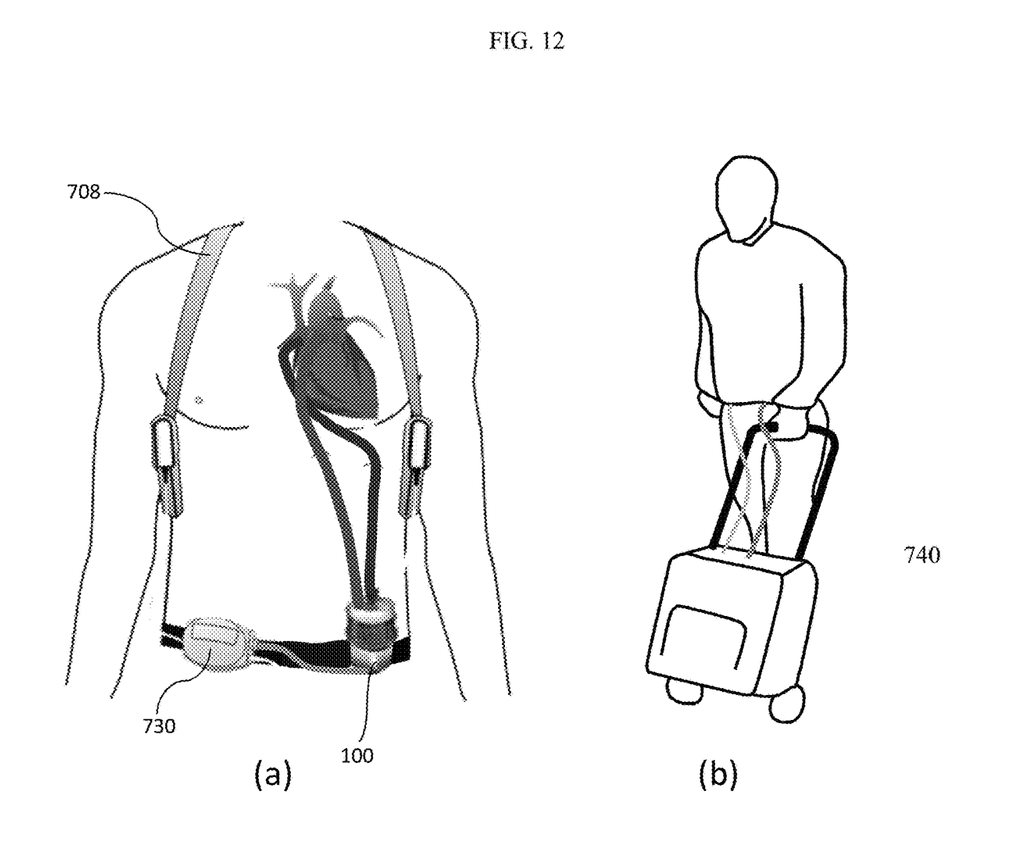
FIG. 12 is a schematic view of the blood oxygenator of FIG. 1 used for ambulatory respiratory/cardiopulmonary support.

Blood oxygenator 100 may likewise be connected to a portable oxygen tank and worn on the user, as depicted in FIG. 12(*a*). In FIG. 12(*a*), straps 708 of a portable oxygen tank are shown, in which case the portable oxygen tank may be positioned on the user's back. The oxygen tank is connected to blood oxygenator 100. Likewise, blood oxygenator 100 and the oxygen tank may be placed inside a cart or bag 740 that the user can manage as shown in FIG. 12(*b*). As shown particularly in FIG. 12(*a*), an oxygen concentrator 730 may be positioned to receive oxygen from the portable oxygen tank and to deliver it to blood oxygenator 100. The oxygen concentrator 730 converts air into high oxygen concentration (>90%) gas. A portable drive console may be provided that can optionally enclose each of the oxygen concentrator 730, a battery power pack, and electronics for the blood pump, flow sensors and blood gas sensors. Kits may be provided that comprise two or more of the components described above.

Blood oxygenator 100 may also optionally include arterial and venous sample ports (not shown) permitting blood samples to be collected by a syringe, such as (by way of non-limiting example) traditional stopcocks or obturator-type sample ports. The sampling ports should provide for the extraction of whole blood from sites before and after the fiber bundle 150 to enable the user to adjust blood flow rates, gas transfer rates and pH for control of oxygen concentration.

Figure 13:
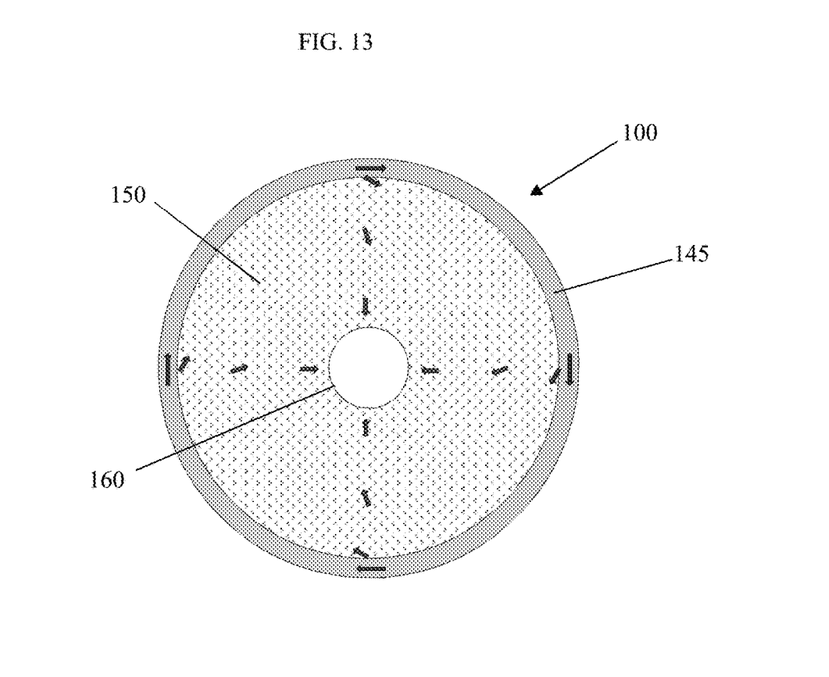
FIG. 13 is a schematic view of a blood flow path in the fiber bundle in the blood oxygenator of FIG. 1.
Figure 14:
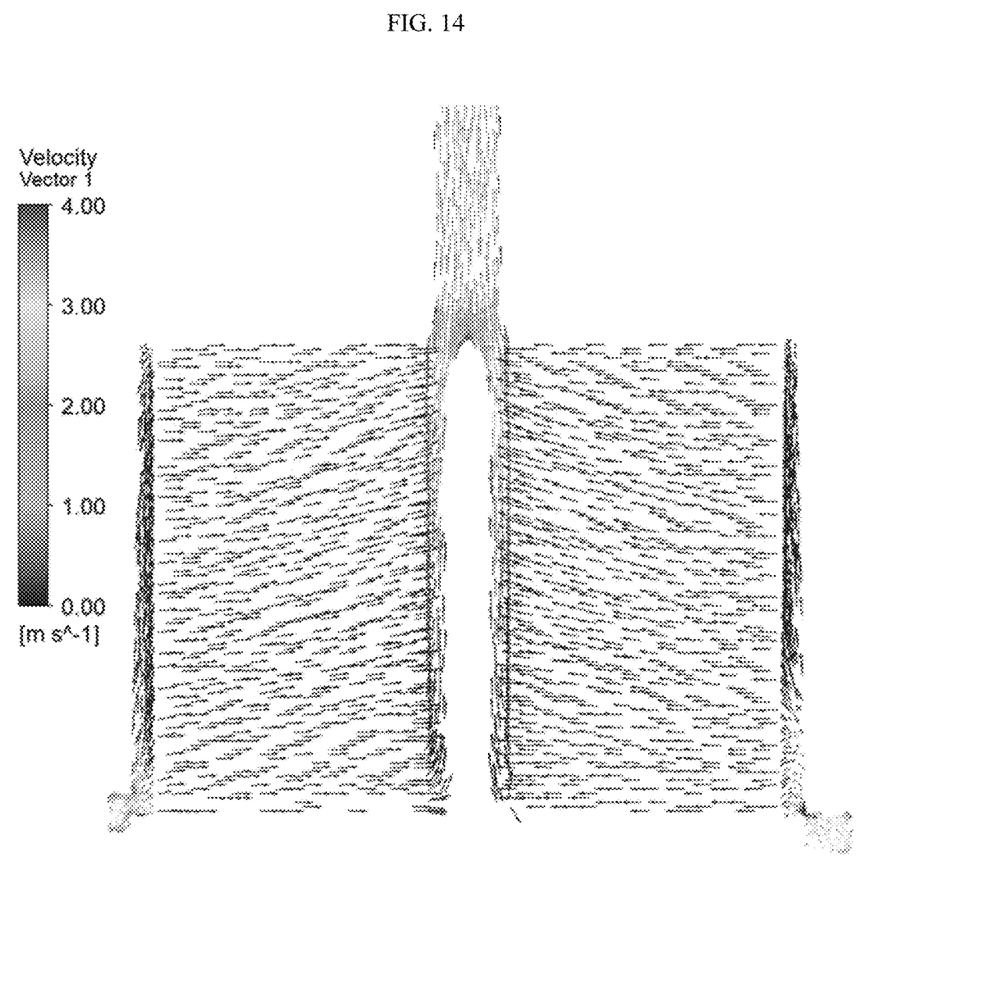
FIG. 14 is a schematic view of a blood flow field in the blood oxygenator of FIG. 1 (4.0 L/min) created from computational fluid dynamics modeling.

The design of the blood oxygenator 100 as configured herein optimizes blood flow. Many of the elements of blood oxygenator 100 that transport patient blood are generally cylindrical or round to promote even flow and reduce turbulence and stagnation. Blood enters the blood inlet 120 with tangential blood velocity relative to the outer surface of the fiber bundle 150. A portion of the blood volume continues to flow in the volute with mainly circumferential velocity, and a portion of the blood volume gradually leaves the volute to enter the annular space 145 with spiral-circumferential velocity. This blood flow discharge mechanism provides a circumferential flow field around the fiber bundle 150 with equal pressure distribution prior to entering the fiber bundle by the spiral volute 140. With this equal pressure distribution, blood radially flows inward through the fiber membranes in the fiber bundle 150. Because the length from the outer surface and inner surface of the fiber bundle 150 is the same 360 degrees around and from the lower potting 152 to the upper potting 154, a uniform blood flow is achieved with minimal pressure loss in the fiber membranes. The existence of the circumferential velocity of the blood around the outer surface of the fiber bundle 150 induces a mixing effect at the initial radial flow through the bundle to reduce the boundary layer of the blood and place red blood cells in closer contact to alleviate $CO_2$ and diffuse $O_2$. Exemplary blood flow paths resulting from the configuration of blood oxygenator 100 as described herein are illustrated in FIGS. 13 and 14.

The design of blood oxygenator 100 also allows for optimized gas flow and diffusion. The lower gas flow chamber 132 receives the sweep gas from the gas inlet 130 and distributes oxygen gas to the open lumen fibers imbedded in potting material (and particularly lower potting 152) of the fiber bundle 150. The oxygen flows through the lumen and diffuses across the outer wall of the individual fiber membranes into the blood, thus allowing blood oxygenation to take place. In parallel, the carbon dioxide from the blood diffuses into the lumen of the fiber membranes and is removed from the blood. The sweep gas flows through the fiber and exits the blood oxygenator 100 through the gas exhaust port 135 in the upper flow chamber 134 of the housing 110 above the upper potting 154. The lower gas flow chamber 132 ensures that a low pressure and uniform sweep gas is established in all the fibers simultaneously. The gas inlet 130 receives the sweep gas to deliver the sweep gas to the interior of blood oxygenator 100.

The blood inflow and outflow connectors may be sized as required for desired blood flow rates and pressures. Typically, such devices are fitted with ¼" or ⅜" barbed fittings receiving standard extracorporeal tubing, although other sizes may be used.

Figure 15:
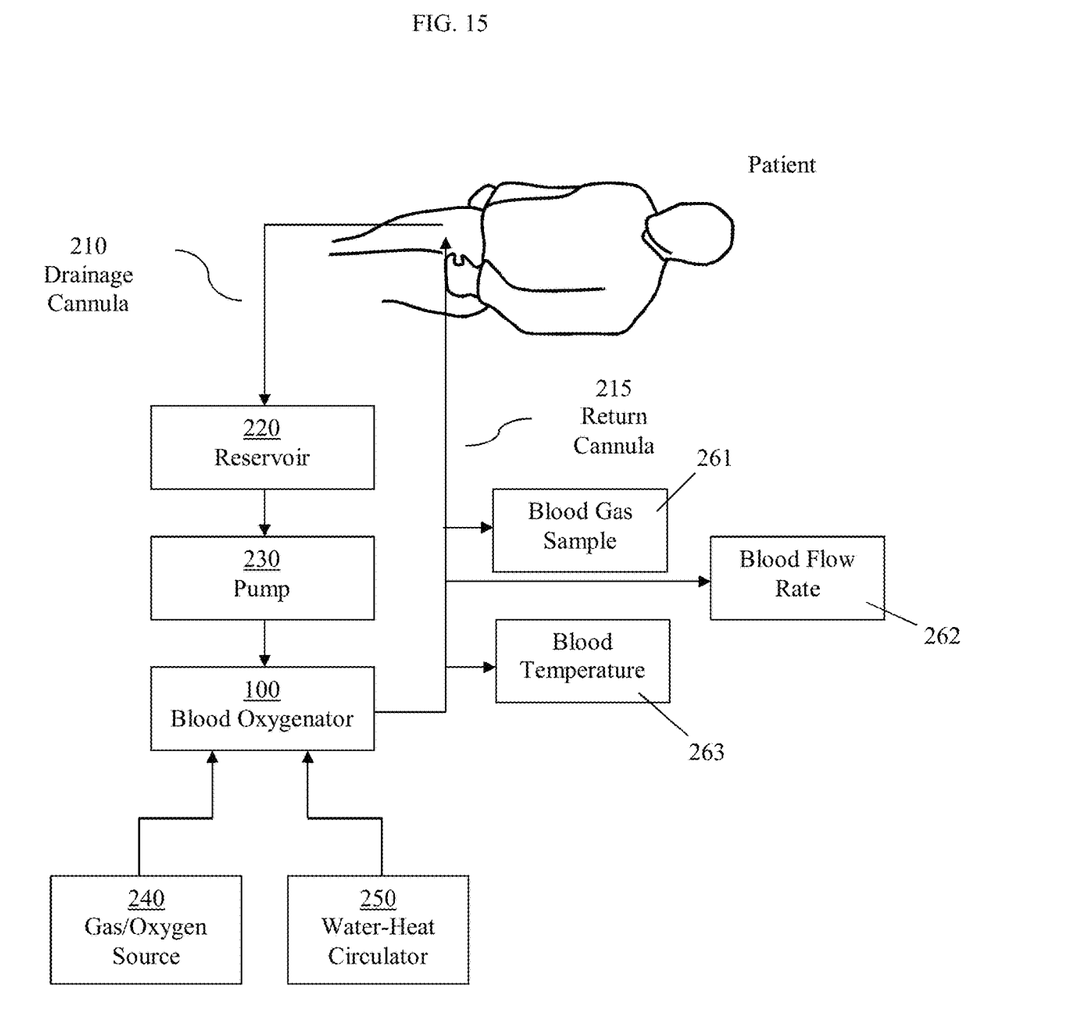
FIG. 15 is a block diagram showing an exemplary setup for the blood oxygenator of FIG. 1 used for cardiopulmonary bypass surgery.

FIG. 15 provides a block diagram depicting one exemplary setup using the blood oxygenator 100. Blood is taken from a patient through drainage cannula 210 and enters into reservoir 220. Blood pump 230 forces blood from the reservoir 220, into blood oxygenator 100 (configured as described above), and back to the patient through return cannula 215. A gas/oxygen source 240 communicates with the blood oxygenator 100 to provide oxygen. A water-heat circulator 250 preferably also communicates with blood oxygenator 100 in those configurations that employ a heat exchange function. Sensors may be used to retrieve information about the blood, such as blood gas concentration sensors 261, blood flow rate sensors 262, and blood temperature sensors 263.

Embodiments may include microporous membranes to filter blood components as utilized in blood dialysis. Further, embodiments may include a filter (e.g., depth filter, reticulated foam, microporous filtration, filtration mediums, etc.) to capture particulate matter as a fluid is driven through the filter.

The blood oxygenator 100 disclosed herein has improved manufacturability over other similar designs of blood oxygenators. It includes fewer components than other blood oxygenating devices. Further, the joints and bonding area may be easily accessed, which makes the blood oxygenator 100 easier, cheaper and more reliable to manufacture.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps.

Furthermore, the indefinite article "a" or "an" is meant to indicate one or more of the item, element or step modified by the article.

What is claimed is:

1. A blood oxygenation system comprising:
a housing having a top and a bottom;
a blood inlet located at a bottom of the housing and a blood outlet located at a top of the housing;
a spiral volute within the housing configured to guide blood from the blood inlet to flow circumferentially around an oxygenator fiber bundle, wherein the oxygenator fiber bundle comprises microporous hollow fibers arranged to form a cylindrical annulus; and
a gas flow chamber configured to distribute oxygen-containing sweep gas into the microporous hollow fibers, wherein the sweep gas facilitates the transfer of oxygen into the blood and the removal of carbon dioxide from the blood.

2. The blood oxygenation system of claim 1, further comprising:
an integrated heat exchanger located adjacent to the oxygenator fiber bundle configured to control the temperature of blood flowing through the oxygenator fiber bundle.

3. The blood oxygenation system of claim 1, wherein the fibers are coated with an anti-thrombogenic agent.

4. The blood oxygenator of claim 3, wherein the anti-thrombogenic agent is heparin.

5. The blood oxygenator of claim 1, wherein the spiral volute is configured to decrease in cross-sectional area from the blood inlet towards the blood outlet to maintain a consistent blood flow velocity.

6. The blood oxygenator of claim 1, further comprising a control system configured to adjust the flow rate of the sweep gas based on the oxygen saturation levels detected in the blood exiting the blood outlet.

7. The blood oxygenator of claim 1, wherein the fiber bundle is configured to have a porosity ranging from 0.4 to 0.7 to optimize the diffusion of gases.

8. A compact blood oxygenator for ambulatory use, comprising:
a cylindrical housing with integrated inlet and outlet ports for blood and gas positioned to facilitate vertical blood flow through the device;
a blood inlet at the lower end of the housing and a blood outlet at the upper end of the housing;
a fiber bundle comprising gas-exchange membranes configured to transfer oxygen to the blood and remove carbon dioxide, wherein the fiber bundle is arranged in a cylindrical configuration within the housing; and
a spiral volute configured to direct blood entering through the blood inlet to flow in a helical pattern around the fiber bundle before passing radially inward through the fiber bundle.

9. The compact blood oxygenator of claim 8, further comprising a heat exchange element integrated within the housing and positioned to regulate the temperature of blood before it enters the fiber bundle, wherein the heat exchange element comprises a series of capillaries that circulate a temperature-controlled fluid.

10. The blood oxygenator of claim 8, wherein the fiber bundle is arranged to provide a radial flow path for the blood from the outer diameter towards the inner diameter of the cylindrical configuration.

11. The blood oxygenator of claim 8, wherein the blood inlet includes a filter configured to remove particulate matter from the blood prior to entering the spiral volute.

12. The blood oxygenator of claim 8, wherein the system is configured for use with a wearable power supply to facilitate ambulatory use.

13. A method for oxygenating blood in an ambulatory setting, comprising:
   providing a blood oxygenator comprising a cylindrical housing, a spiral volute, a fiber bundle with gas-exchange membranes, and an integrated heat exchanger;
   introducing blood into the blood oxygenator through a blood inlet at a bottom of the housing;
   directing the blood to flow helically around the fiber bundle via the spiral volute to ensure uniform distribution of blood across the fiber bundle;
   transferring oxygen to the blood and removing carbon dioxide from the blood via the gas-exchange membranes as the blood flows radially through the fiber bundle;
   regulating the temperature of the blood using the integrated heat exchanger before the blood contacts the fiber bundle; and
   discharging the oxygenated and temperature-regulated blood from a blood outlet at a top of the housing.

14. The method of claim 13, wherein the step of introducing blood into the blood oxygenator includes pre-filtering the blood to remove debris before it enters the blood inlet.

15. The method of claim 13, wherein the step of transferring oxygen to the blood and removing carbon dioxide includes adjusting the flow rate of the sweep gas based on real-time blood gas analysis results.

16. The method of claim 13, wherein the step of regulating the temperature of the blood uses a feedback system that adjusts the temperature based on continuous temperature measurements of the blood exiting the blood oxygenator.

* * * * *